(12) United States Patent
Giambattista et al.

(10) Patent No.: US 10,166,344 B2
(45) Date of Patent: Jan. 1, 2019

(54) INJECTION NEEDLE ASSEMBLY

(71) Applicant: SHL Group AB, Nacka Strand (SE)

(72) Inventors: Lucio Giambattista, East Hanover, NJ (US); David De Salvo, Lake Hiawatha, NJ (US); Antonio Bendek, Vernon, NJ (US)

(73) Assignee: SHL GROUP AB, Nacka Strand (SE)

( * ) Notice: Subject to any disclaimer, the term of this patent is extended or adjusted under 35 U.S.C. 154(b) by 0 days.

(21) Appl. No.: 15/419,113

(22) Filed: Jan. 30, 2017

(65) Prior Publication Data

US 2017/0136191 A1    May 18, 2017

Related U.S. Application Data

(62) Division of application No. 13/847,541, filed on Mar. 20, 2013, now Pat. No. 9,687,615, which is a division
(Continued)

(30) Foreign Application Priority Data

Dec. 1, 2008  (SE) ..................... 0850110

(51) Int. Cl.
*A61M 5/32* (2006.01)
*A61M 5/34* (2006.01)
*A61M 5/24* (2006.01)

(52) U.S. Cl.
CPC ........ *A61M 5/3204* (2013.01); *A61M 5/3202* (2013.01); *A61M 5/3286* (2013.01);
(Continued)

(58) Field of Classification Search
CPC ............. A61M 5/3202; A61M 5/3204; A61M 5/3293; A61M 5/34; A61M 5/347;
(Continued)

(56) References Cited

U.S. PATENT DOCUMENTS 2,677,373 A   5/1954  Barradas
2,828,742 A   4/1958  Ashkenaz
(Continued)

FOREIGN PATENT DOCUMENTS

EP   2022522   2/2009
GB   1191634   5/1970
GB   2424836   10/2006

OTHER PUBLICATIONS

International Search Report for corresponding International Application No. PCT/EP2009/056750, dated Sep. 10, 2009.
Written Opinion for corresponding International Application No. PCT/EP2009/056750, dated Sep. 10, 2009.

*Primary Examiner* — Kami A Bosworth
(74) *Attorney, Agent, or Firm* — McDonnell Boehnen Hulbert & Berghoff LLP

(57) ABSTRACT

An injection needle assembly is presented having an injection needle where the distal pointed end is arranged to penetrate a membrane arranged at the proximal end of a medicament container; a tubular needle holder having a distal engagement means and proximal engagement means; a tubular cap having a proximal outer engagement means and proximal inner engagement means; a tubular needle cover comprising first engagement means arranged to cooperate with the proximal engagement means, and second engagement means arranged to cooperate with the proximal outer engagement means of the cap. The needle cover is arranged to be displaced from a first position wherein the second engagement means and the proximal outer engagement means prevents the needle cover and the needle holder to be axially displaced by a linear displacement, to a second position wherein the needle cover and the needle holder are distally displaced.

5 Claims, 8 Drawing Sheets

Related U.S. Application Data of application No. 12/996,837, filed as application No. PCT/EP2009/056750 on Jun. 2, 2009, now Pat. No. 8,708,970.

(60) Provisional application No. 61/060,191, filed on Jun. 10, 2008.

(52) U.S. Cl.
CPC ........... A61M 5/347 (2013.01); A61M 5/2466 (2013.01); A61M 2005/2474 (2013.01)

(58) Field of Classification Search
CPC .. A61M 2005/2488; A61M 2039/1033; A61M 2039/1038
See application file for complete search history.

(56) References Cited

U.S. PATENT DOCUMENTS

| | | | |
|---|---|---|---|
| 3,021,942 A * | 2/1962 | Hamilton | A61M 5/3202 206/365 |
| 3,916,893 A | 11/1975 | De Felice | |
| 3,967,621 A | 7/1976 | Schwarz | |
| 4,976,701 A * | 12/1990 | Ejlersen | A61M 5/24 206/365 |
| 5,658,259 A | 8/1997 | Pearson et al. | |
| 5,718,690 A | 2/1998 | Gettig | |
| 6,743,203 B1 | 6/2004 | Pickhard | |
| 7,374,558 B2 | 5/2008 | Kirchhofer | |
| 2003/0144633 A1 | 7/2003 | Kirchhofer | |
| 2005/0033268 A1 | 2/2005 | Decaria | |

* cited by examiner

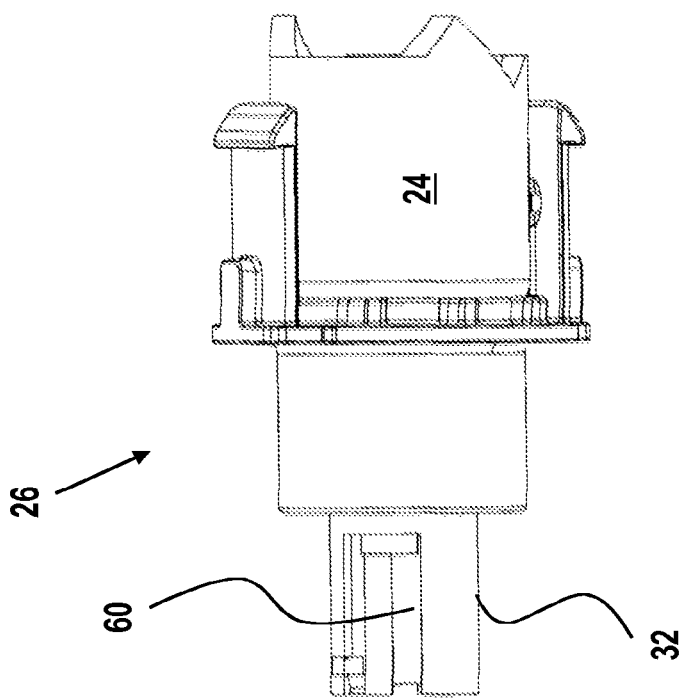
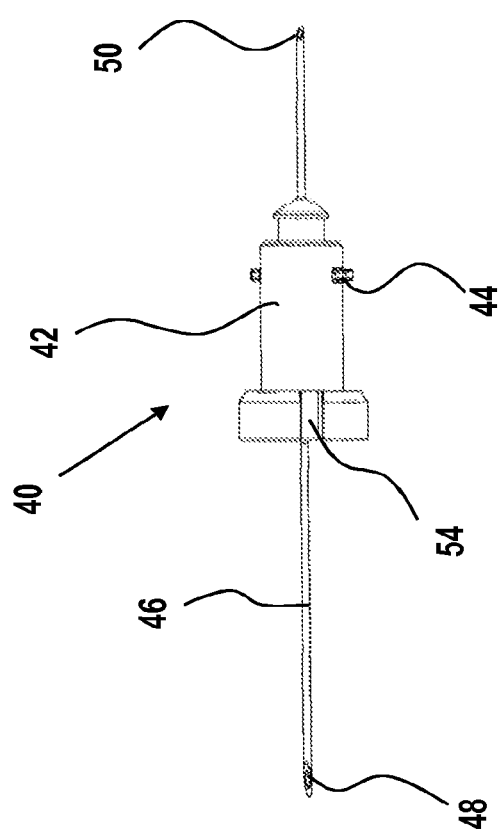
Fig. 3

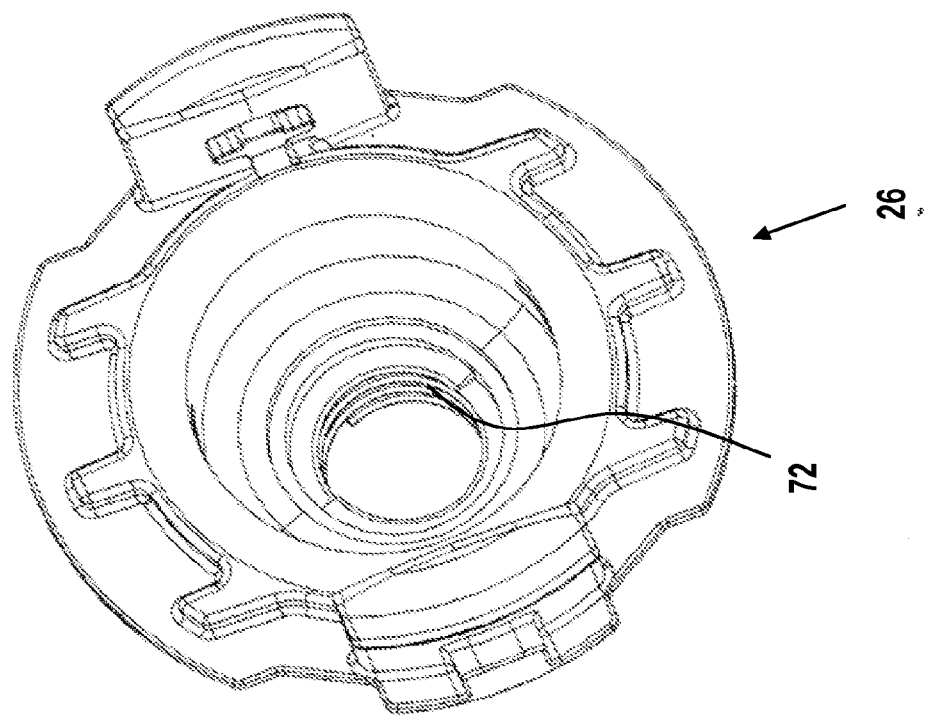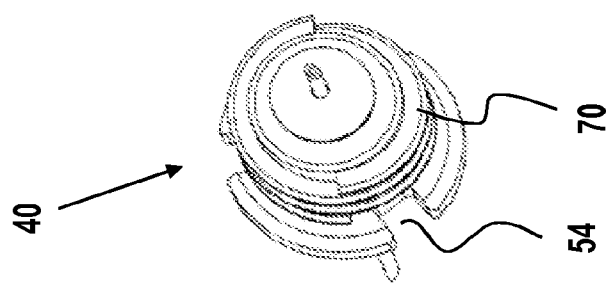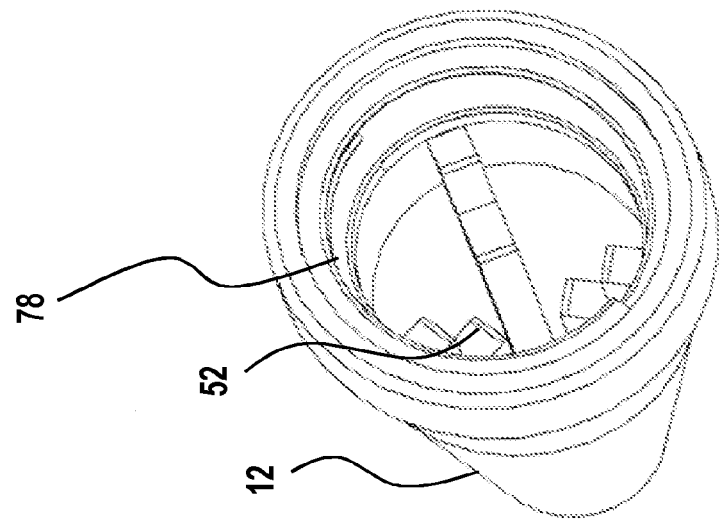
Fig. 8

INJECTION NEEDLE ASSEMBLY

CROSS REFERENCE TO RELATED APPLICATIONS

The present application is a division of U.S. patent application Ser. No. 13/847,541,filed Mar. 20, 2013, now U.S. Pat. No. 9,687,615, which is a division of U.S. patent application Ser. No. 12/996,837, filed Jan. 25, 2011, now U.S. Pat No. 8,708,970, which is a U.S. National Phase Application pursuant to 35 U.S.C. § 371 of International Application No. PCT/EP2009/056750 filed Jun. 2, 2009, which claims priority to U.S. Provisional Patent Application No. 61/060,191 filed Jun. 10, 2008 and Swedish Patent Application No. 0850110-8 filed Dec. 1, 2008. The entire disclosure contents of these applications are herewith incorporated by reference into the present application.

FIELD OF THE INVENTION

The present invention relates to an injection needle for medical devices, and in particular sterile aspects of handling injection needles.

BACKGROUND

Many medicament delivery devices such as injectors are often developed for self-administration, i.e. the user performs the injection. In order to have a simple handling of the device it is often desirable to have it as pre-assembled as possible. Therefore often the injector is delivered to the user with an injection needle pre-attached.

Another aspect of attachment of injection needles to medicament containers is that the rear end of the injection needle often protrudes into the interior of the container. This could be a drawback if the medicament reacts with the material of the needle when exposed for a period of time. In that respect it would be desirable to have the rear part of the needle outside the container until the injection is to be performed. On the other hand, this then requires that the rear end of the needle could be moved fairly easily into the container and also that the rear end of the needle is kept in a sterile environment until it is moved into the container.

A few attempts have been done to solve this problem. Document U.S. Pat. No. 7,374,558 discloses an auto-injector having drive means for automatic penetration and injection. At the front end of the injector a sealed compartment is arranged, in which a sterile injection needle is arranged. When the injector is activated, the medicament container is pushed forward, whereby a membrane at the front end of the container is penetrated by the rear end of the needle. After this the container and the needle is advanced further, causing a penetration of the patient's skin. After penetration the injection is performed automatically.

Documents U.S. Pat. Nos. 6,743,203 and 5,658,259 disclose similar auto-injectors having a needle positioned in a sterile compartment at the front end of the injector, and where the rear of the needle penetrates the medicament container upon activation in that the container is pushed forward. Subsequent steps are penetration and injection.

The above mentioned injectors require a lot of components and it is relatively complicated to sterilize the injection needle and keep it sterile. Further, for multi-dose injectors requiring a needle change before each injection, the above mentioned solutions cannot be used.

Documents U.S. Pat. Nos. 2,828,742 and 3,916,893 disclose injectors having needles that are attached into a proximal neck portion of a medicament container such that a distal end of the injection needle penetrates a membrane of the medicament container when a needle holder is distally displaced. One of the reasons for the design according to '742 and '893 is to keep a zone sterile between the medicament container and the needle. In '742, the needle holder is distally displaced by merely gripping a surrounding needle sheath that is of a flexible material, such as rubber, thereby providing a risk of accidental needle sticks. Further, there is no locking/preventing means between the sheath and the cap/ferrule, which is a disadvantage if a user/patient removes the sheath before the distal end of the injection needle penetrates the membrane, since the proximal end of the needle may be contaminated or/and it may be difficult to position the sheath again in connection with the cap/ferrule. In '893, the needle holder is distally displaced by threading the sheath in one direction onto a cap/syringe body. There are no locking/preventing means between the needle holder and the cap/syringe body after the needle holder has been distally displaced. This is a disadvantage if the press fitting between the needle holder and the cap/syringe body is not enough to withstand the pressure exerted when expelling a liquid. Moreover, the removal of the sheath is not either intuitive since the user/patient has to rotate the sheath back to remove it.

SUMMARY

The aim of the present invention is to provide an injection needle assembly comprising an injection needle that is kept sterile until use, which is kept out of contact with the medicament until use, and which assembly is secure and easy to handle for a patient.

This aim is obtained by the injection needle assembly characterised by the features of the independent patent claims. Preferable embodiments of the present invention are the subject of the dependent patent claims.

According to a main aspect of the invention, it is characterised by a needle assembly having opposite distal and proximal ends, the assembly comprises an injection needle having proximal and distal pointed ends, wherein the distal pointed end is arranged to penetrate a membrane arranged at the proximal end of a medicament container; a tubular needle holder partially surrounding and fixedly connected to said injection needle, wherein said needle holder comprises on its outer circumferential surface distal engagement means and proximal engagement means; a tubular cap comprising a distal part having container attachment means, a proximal part having proximal outer engagement means on its outer circumferential surface, and a central passage having proximal inner engagement means on its inner circumferential surface adapted for receiving the distal engagement means of the needle holder; a tubular needle cover comprising on its inner circumferential surface, first engagement means arranged to cooperate with the proximal engagement means of the needle holder, and second engagement means arranged to cooperate with the proximal outer engagement means of the cap; wherein said needle cover is arranged to be displaced from a first position wherein the second engagement means and the proximal outer engagement means prevents the needle cover and the needle holder to be axially displaced by a linear displacement, to a second position wherein the needle cover and the needle holder are distally displaced, and wherein the proximal inner engagement means of the cap and the distal engagement means of the needle holder prevents the needle holder to be proximally displaced but allows the needle cover to be distally displaced.

According to another aspect of the invention, the second engagement means of the needle cover and the proximal outer engagement means of the cap; and the proximal inner engagement means of the cap and the distal engagement means of the needle holder are bayonet fittings.

According to a further aspect of the invention, the second engagement means of the needle cover and the proximal outer engagement means of the cap; and the proximal inner engagement means of the cap and the distal engagement means of the needle holder are threaded engagements.

According to yet an aspect of the invention, the distal part of the cap is either attached to the proximal end of the container or attached to both the proximal end of the container and to a housing part or container holder of a delivery device by the container attachment means.

According to one aspect of the invention, the distal pointed end of the injection needle is kept sterile by the protective cover.

There are a number of advantages with the present invention. Because the needle assembly comprises three components, the cap, the needle holder, and the needle cover, wherein the cap and needle holder are displaceable and lockable in relation to each other, and wherein the cap and the needle cover are displaceable and lockable in relation to each other; the injection needle could easily be moved from one position where it is not in contact with medicament, but kept in a sterile environment, to a position where it is in contact with the medicament, which preferably is just before injection by the patient. Preferably the displacement of the holder is performed by the needle cover, which then has multiple functions, i.e. covering the needle from accidental needle sticks, keeping the needle sterile and displacing the needle in contact with the medicament such that an injection may be performed.

In order to ascertain the protection of the needle from the environment the needle cover is preferably press-fitted onto the cap, thereby ensuring the sterility of the needle. The locking of the cap and the needle cover in relation could preferably be performed by mechanical locking means such as bayonet fittings or threads, which are locking means that easily could be performed by handling of the needle cover.

Apart from the injection needle assembly the present invention naturally also comprises a medicament container arranged with the needle assembly.

These and other aspects of and advantages with the present invention will become apparent from the following detailed description and from the accompanying drawings.

BRIEF DESCRIPTION OF THE FIGURES

In the following detailed description of the invention, reference will be made to the accompanying drawings, of which FIG. 3 shows a side exploded view of FIG. 2, FIG. 8 shows perspective views of the needle cover, of the needle holder and of the cap of FIG. 6 seen from their distal ends.

DETAILED DESCRIPTION

Figure 1:
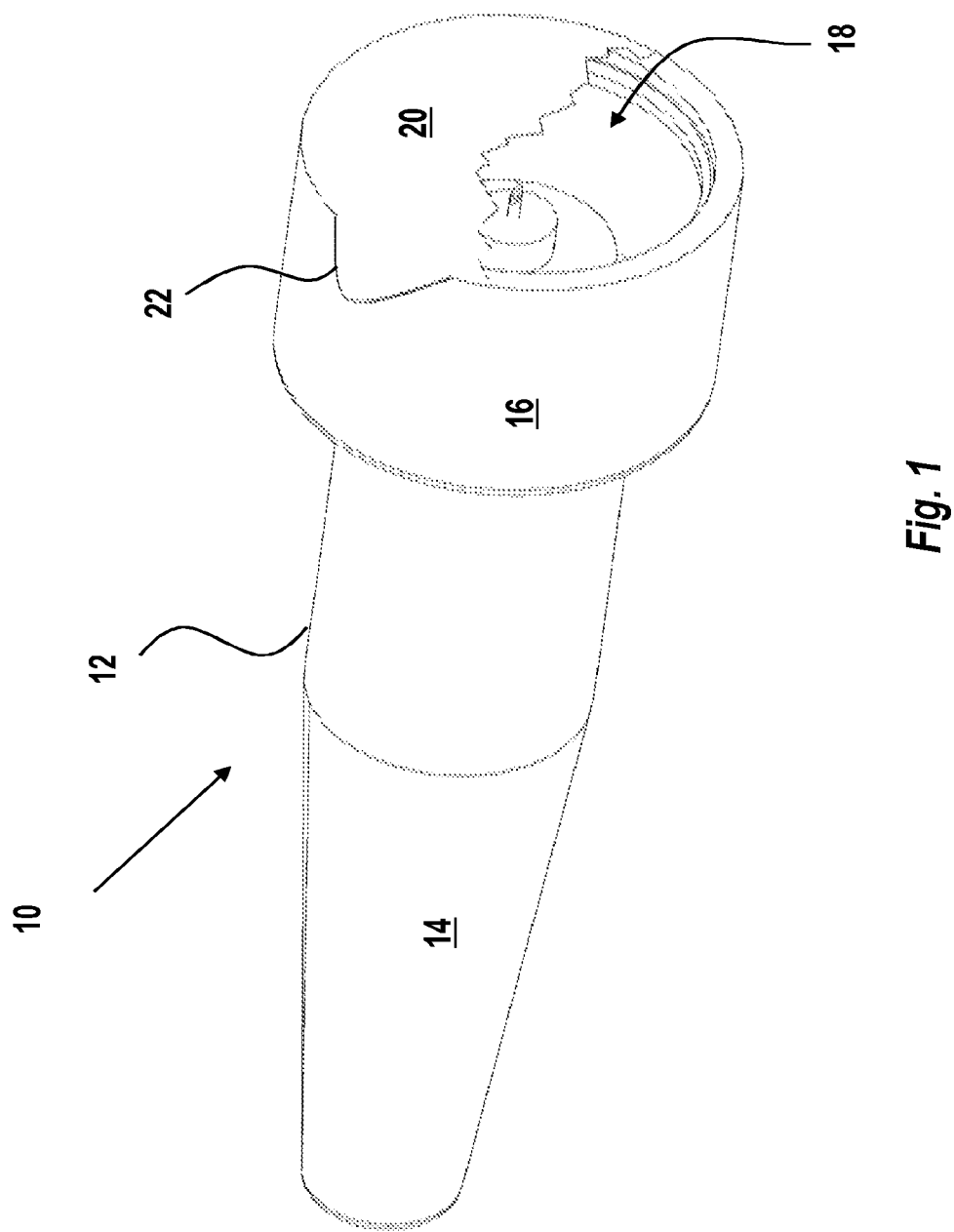
FIG. 1 shows perspective view of a needle cover and of a protective cover of the needle assembly of the present invention.
Figure 2:
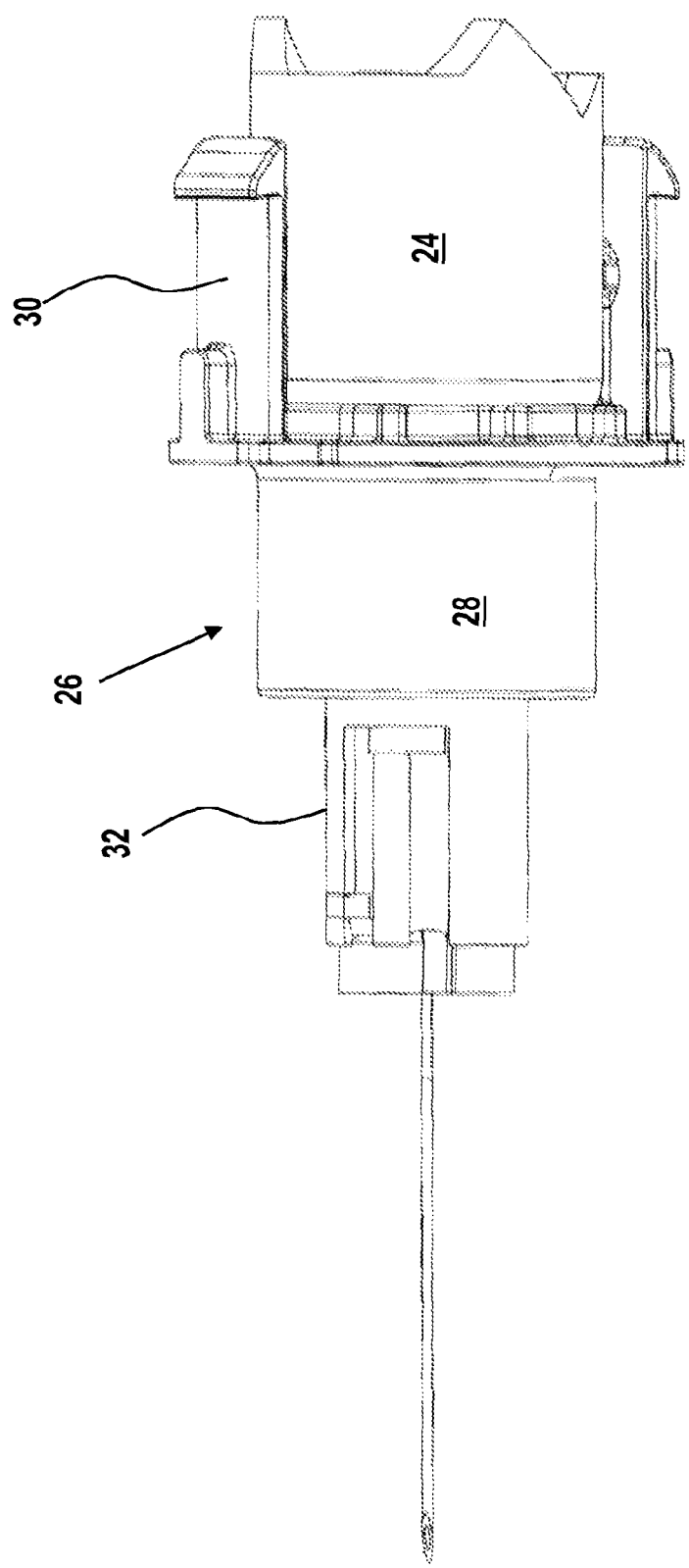
FIG. 2 shows a side view of a tubular cap and of a needle holder of FIG. 1 without the needle cover.

In the present application, when the term "distal part/end" is used, this refers to the part/end of the assembly, or the parts/ends of the members thereof, which is/are located the furthest away from the medicament delivery site of the patient. Correspondingly, when the term "proximal part/end" is used, this refers to the part/end of the assembly, or the parts/ends of the members thereof, which, is/are located closest to the medicament delivery site of the patient.

The present invention is intended to be used in medicament injection devices, which could be of any type from simple manual injectors to multi-function auto-injectors. However they do not form part of the present invention and are thus not shown in the drawings.

FIG. 1 shows a needle assembly 10 having opposite distal and proximal ends according to the present invention. The assembly comprises an injection needle 46 having proximal 48 and distal 50 pointed ends, wherein the distal pointed end is arranged to penetrate a membrane (not shown) arranged at the proximal end of a medicament container 24; a tubular needle holder 40 partially surrounding and fixedly connected to said injection needle 46, wherein said needle holder comprises on its outer circumferential surface distal engagement means 44; 70 and proximal engagement means 54; a tubular cap 26 comprising a distal part 28 having container attachment means 30, a proximal part 32 having proximal outer engagement means 60; 80 on its outer circumferential surface, and a central passage 34 having proximal inner engagement means 36, 38; 72 on its inner circumferential surface adapted for receiving the distal engagement means 44; 70 of the needle holder; a tubular needle cover 12 comprising on its inner circumferential surface, first engagement means 52 arranged to cooperate with the proximal engagement means 54 of the needle holder, and second engagement means 58; 78 arranged to cooperate with the proximal outer engagement means 60; 80 of the cap; wherein said needle cover is arranged to be displaced from a first position wherein the second engagement means 58; 78 and the proximal outer engagement means 60; 80 prevents the needle cover and the needle holder to be axially displaced by a linear displacement, to a second position wherein the needle cover and the needle holder are distally displaced, and wherein the proximal inner engagement means 36, 38; 72 of the cap and the distal engagement means 44; 70 of the needle holder prevents the needle holder to be proximally displaced but allows the needle cover to be distally displaced.

The needle cover 12 comprises a slightly conical proximal part 14, a generally tubular distal part 16 and a central tubular part between them, where the tubular distal part 16 has a somewhat larger diameter than the central tubular part.

Figure 4:
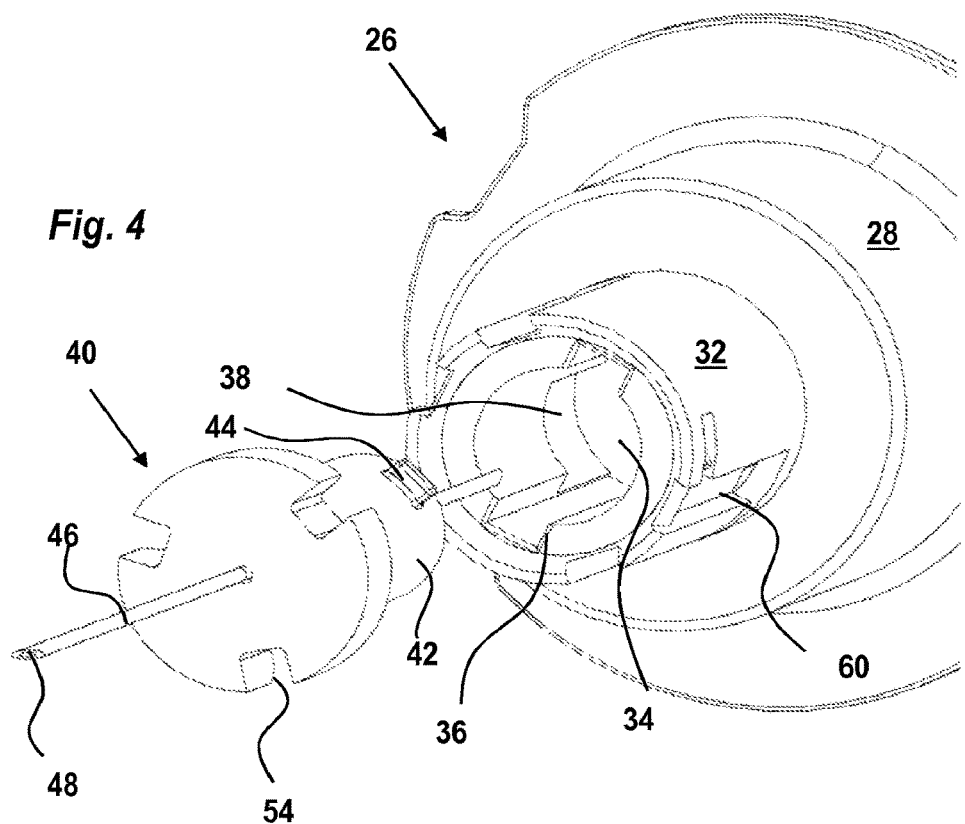
FIG. 4 shows a perspective exploded view of FIG. 2.

The cap 26 is tubularly shaped and thus has the central passage 34, FIG. 4. The proximal inner engagement means on the central passage are at least one longitudinally extending groove 36 ending in a generally transversal groove 38, thereby forming a general T-shape, thus creating one part of a bayonet fitting, FIG. 4.

The outer diameter of the distal end 42 of the needle holder generally corresponds as the inner diameter of the passage 34, and is arranged with the distal engagement means as e.g. ledges 44, creating the other part of the bayonet fitting, intended to cooperate with the grooves 36, 38; FIG. 4.

Figure 5:
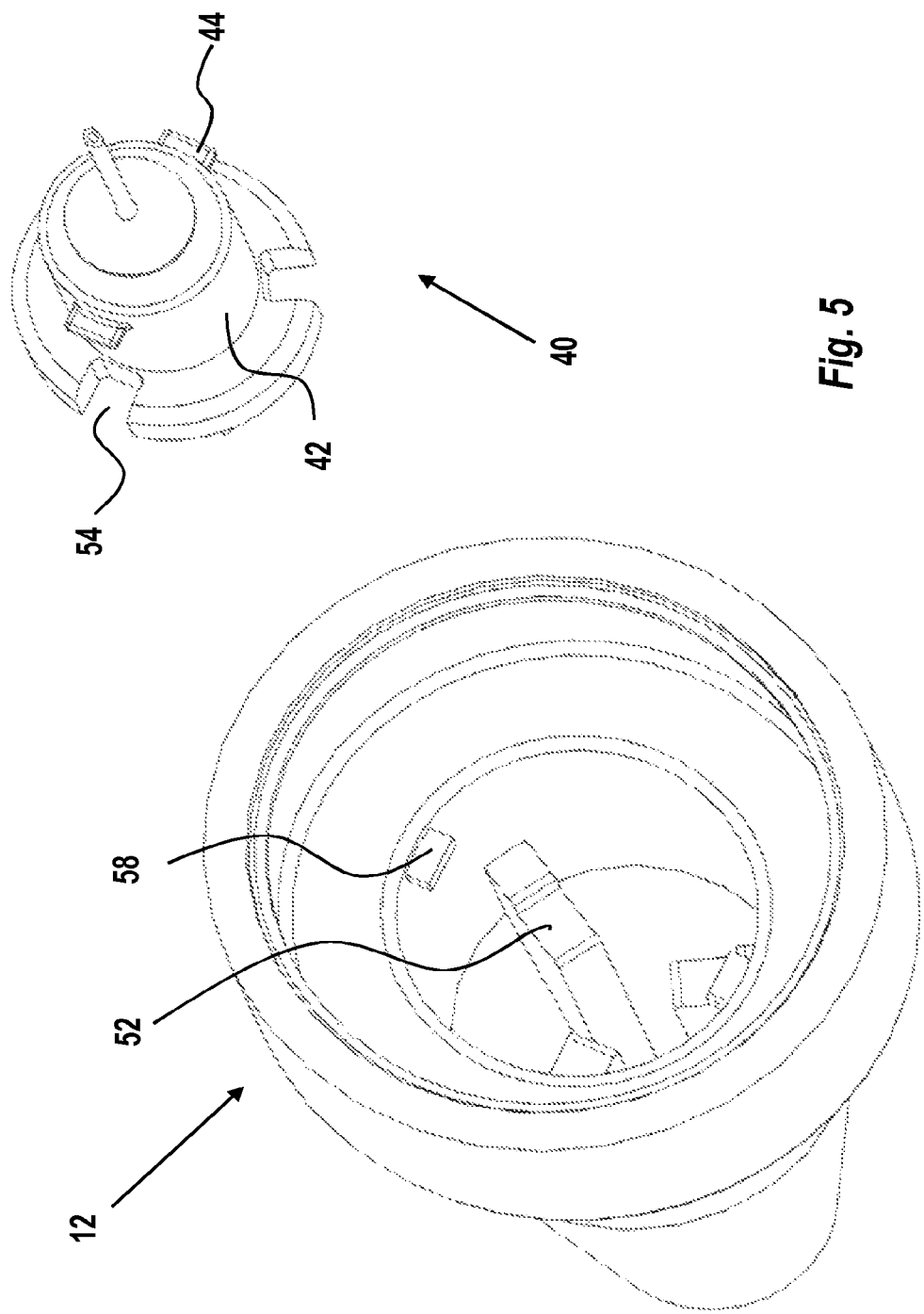
FIG. 5 shows a perspective views of the needle cover and of the needle holder of FIG. 2 seen from their distal ends.

The tubular distal part 16 of the needle cover has a diameter that surround the container attachment means and the central part of the needle cover has an inner diameter somewhat larger than the outer diameter of the distal tubular part 28 of the cap 26, but such that central part of the needle cover is press fitted onto the distal tubular part 28 of the cap. The inner circumferential surface of the distal tubular part of the needle cover is provided with the first engagement means as e.g. three axially extending ledges, where each has a first radial inwardly directed ledge 52, FIG. 5. These ledges 52 fit into the proximal engagement means of the needle holder e.g. cut-outs 54. Further the inner circumferential surface of the distal tubular part of the needle cover is arranged with the second engagement means 58 as e.g. an inwardly directed ledge, which is intended to fit into the proximal outer engagement means 60 of the cap as e.g. an -shaped groove having a first transversal part, a first longitudinal part, a second transversal part and a second longitudinal part.

The distal part 28 of the cap 26 is either attached to the proximal end of the container or attached to both the proximal end of the container and to a housing part or container holder of a delivery device by the container attachment means 30.

When the needle assembly is delivered to the user a portion of the distal part of the needle holder is partially press fitted into the cap and the radial distal front surface of the distal engagement means 44 of the needle holder abuts the radial proximal surface of the proximal part 32 of the cap. Also, the inwardly directed ledge 58 of the needle cover 12 is in engagement with the first transversal part of the bayonet fitting groove 60 and thereby an axial movement of both the needle holder and the needle cover is prevented.

For penetrating the membrane of the container with the distal pointed end 50 of the needle 46, the user twists the needle cover 12, whereby the needle holder 40 also twists due to the connection between them via the inwardly directed ledges 52 fitting into the cut-outs 54 of the needle holder. This twisting also causes the inwardly directed ledge 58 of the needle cover 12 to move out of the first transversal part of the bayonet fitting groove 60 on the outside of the cap 26, and the ledges 44 of the needle holder 40 to fit into the longitudinal grooves 36 of the cap 26, thereby enabling both the needle cover 12 and the needle holder to be linearly pushed towards the distal end of the assembly. During the linear motion of the needle holder into the cap, the distal pointed end 50 of the injection needle 46 penetrates the membrane of the medicament container, thereby creating a passage from the interior of the container to the proximal pointed end 48 of the injection needle 46.

When the ledges 44 have reached the end of the longitudinal grooves 36 the user twists further the needle cover 12, whereby the needle holder 40 also twists due to the connection between them via the inwardly directed ledges 52 fitting into the cut-outs 54 of the needle holder. The further twisting then causes the ledges 44 to fit into the transversal groove 38, thereby causing a bayonet locking of the needle holder with the cap whereby the needle holder cannot be axially displaced. The further twisting also causes and the inwardly directed ledge 58 of the needle cover 12 to move through and out of the second transversal part of the bayonet fitting groove 60 on the outside of the cap 26. Now, the needle cover 12 may be pulled off the needle holder 40 and the cap 26. The injection needle assembly is now ready for injection.

Figure 6:
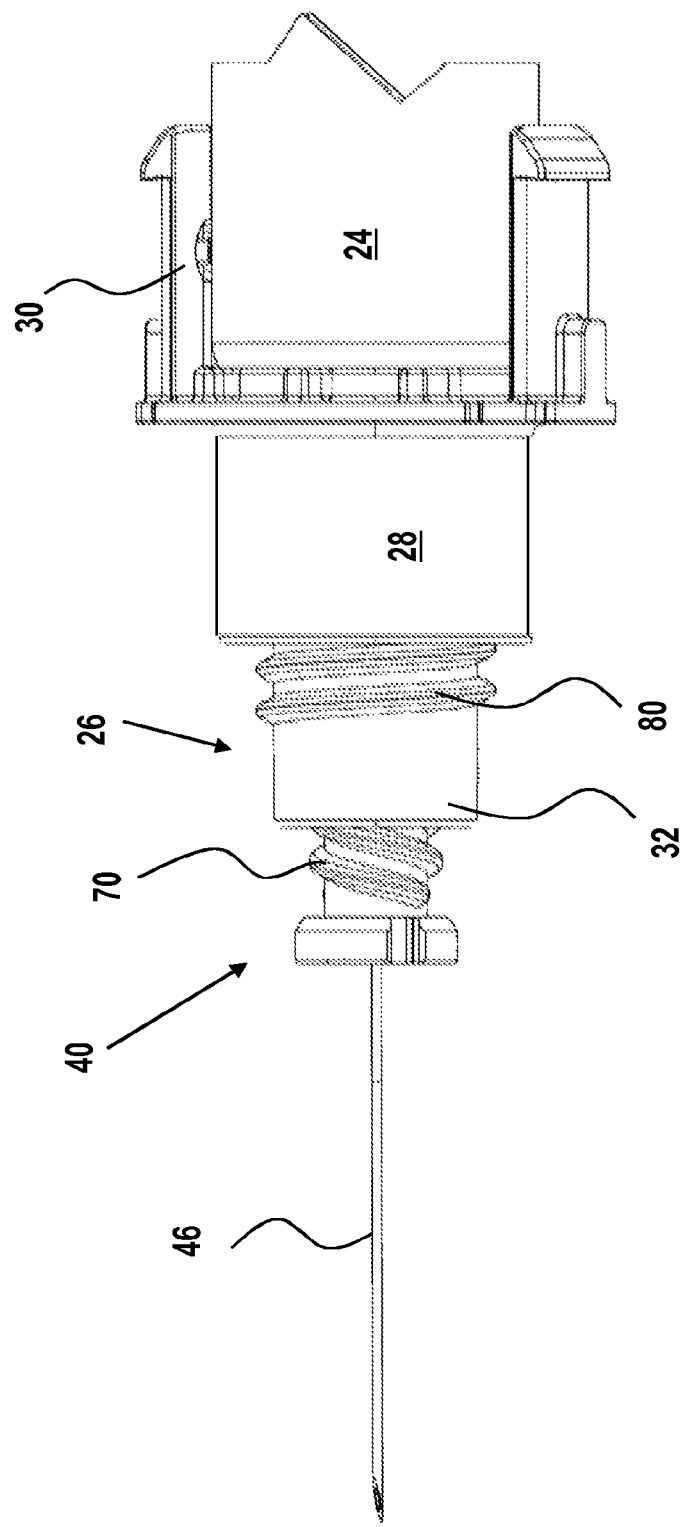
FIG. 6 shows a side view of a tubular cap and of a needle holder of a variant of the needle assembly.
Figure 7:
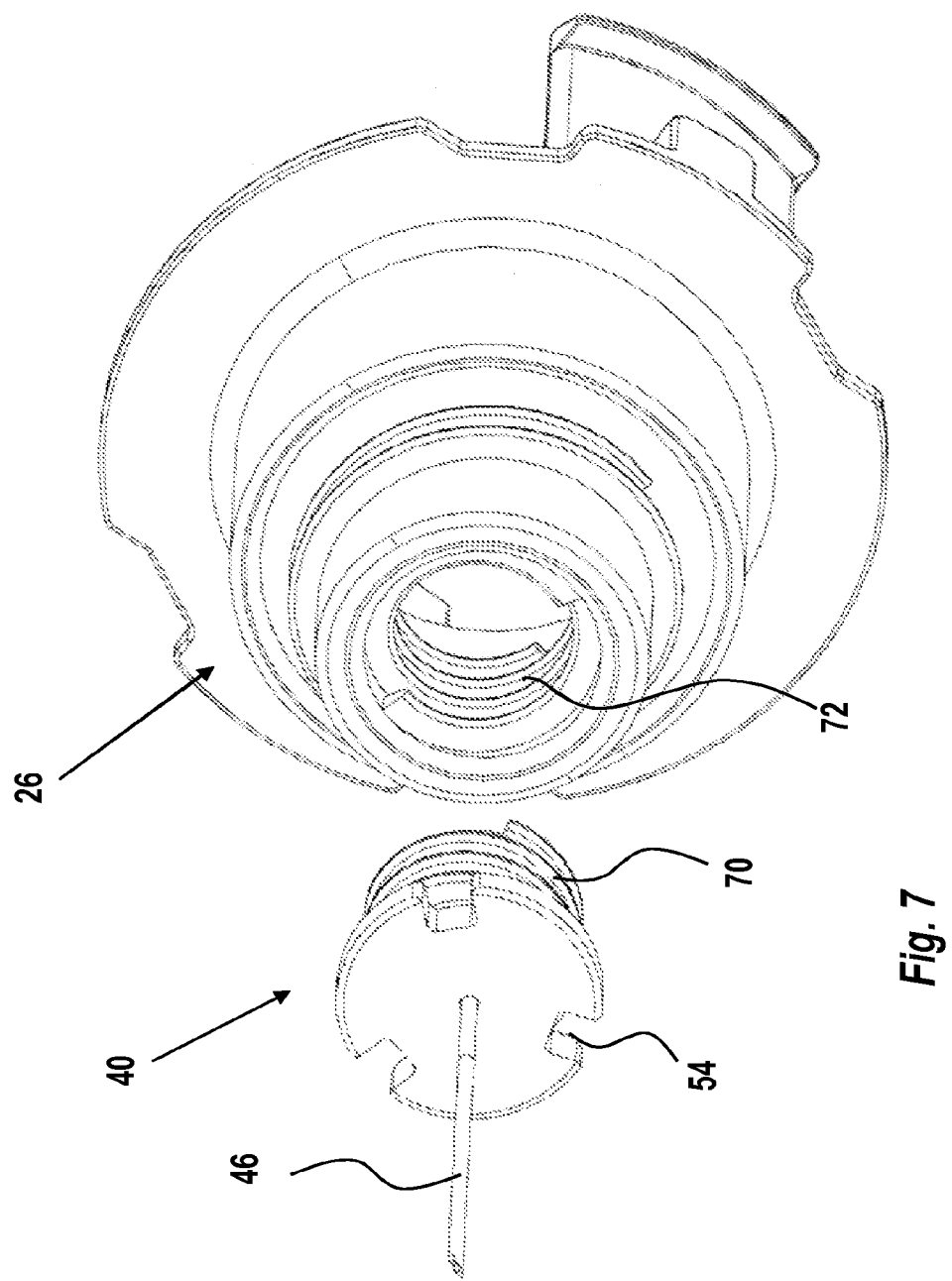
FIG. 7 shows a perspective exploded view of FIG. 6.

FIGS. 6-8 show a variant of the embodiment of FIG. 1. Instead of bayonet fittings between the needle holder and the cap, and between the needle cover and the cap, the distal engagement of the needle holder 70 and the proximal inner engagement means 72 of the cap are threads 70, and the proximal outer engagement means 80 of the cap and the second engagement means 78 of the needle cover are also threads. Thus, when the needle cover is turned, the needle holder is screwed into the cap, which movement causes the distal pointed end 50 of the injection needle 46 to penetrate the membrane of the medicament container. It is however to be noticed that the threads 80, 78 between the needle cover and the cap, has a different direction of the pitch than the threads 70, 72 between the needle holder and the cap.

When the needle assembly is delivered to the user the needle cover is partially screwed onto the cap and the needle holder is also partially screwed into the cap as shown in FIG. 6, with just a few threads in engagement with the cap. When the user then starts to turn the needle cover, this turning causes the needle holder to be screwed into the cap whereby the pointed distal end of the injection needle penetrates the membrane of the medicament holder and due to the different direction of the pitch the needle cover is screwed off the cap and may be removed. Preferably the pitches of the threads are chosen such that there is a major longitudinal movement of the needle holder into the cap for a small turning angle in order to prevent as much as possible turning or "drilling" of the distal end of the injection needle in the membrane. At the same time the pitch of the threads between the needle cover and the hub is preferably chosen such that the user only needs to turn the needle cover about half a turn in order to perform the operation so as to avoid having to change grip in order to finish the operation.

In the previous embodiments, the cap 26 has previously been attached in a proper manner to the proximal end of the medicament container in a sterile form.

In another embodiment, the injection needle assembly according to the present invention has the appearance of FIG. 1. Thus the distal pointed end of the injection needle is kept sterile by a protective cover 20, such as an aluminium foil or plastic foil or the like arranged on a distal opening 18 of the needle cover. The protective cover 20 is preferably arranged with a grip means, such as a tab 22, for facilitating the removal of the protective cover. When the injection needle assembly is to be attached to the medicament container/injection device, the protective cover is torn away and the needle cap is attached to the container and to the delivery.

It is to be understood that the embodiment described above and shown in the drawings is to be regarded only as a non-limiting example of the invention and that it may be modified in many ways within the scope of the patent claims.

The invention claimed is:

1. An injection needle assembly having opposite distal and proximal ends, comprising:
   (a) a tubular needle cover comprising,
      an open distal end having an inner diameter;
      an inner circumferential surface having,
         a plurality of axially extending ledges; and
         a first thread having a first pitch in a first direction;

(b) a tubular needle holder comprising, an injection needle; and an outer circumferential surface having two separate engagement devices, the first engagement device comprising cut-outs configured to engage the axially extending ledges of the needle cover and the second engagement device comprising a second thread having a second pitch in a second direction; and (c) a tubular cap comprising, an outer circumferential surface having a third thread that engages the first thread of the needle cover, a central passage having a diameter larger than the outer circumferential surface of the tubular needle holder and a fourth thread configured to engage the second thread of the needle holder, wherein the third thread is configured to threadedly engage a proximal end of a container attachment device that operatively connects to a proximal end of a medicament container, wherein the inner diameter of the open distal end of the needle cover completely encloses the needle holder and the cap, where a protective cover seals the open distal end to maintain sterility of the needle.

2. The needle assembly of claim 1, wherein the first direction of the first pitch is opposite of the second direction of the second pitch.

3. The needle assembly of claim 1, wherein the first pitch of the first thread is the same as the second pitch of the second thread.

4. The needle assembly of claim 1, further characterized in that the first thread is partially engaged with the third thread and the second thread is partially engaged with the fourth thread when the needle holder and the cap are sealed within the needle cover by the protective cover.

5. The needle assembly of claim 1, wherein the container attachment device is configured for attachment to a container holder of a drug delivery device.

* * * * *